(12) United States Patent
Taylor

(10) Patent No.: US 6,557,182 B2
(45) Date of Patent: May 6, 2003

(54) ULTIMATE WARE

(76) Inventor: Charles Taylor, Rte. 1 Box 186, Berry, KY (US) 41003

( * ) Notice: Subject to any disclaimer, the term of this patent is extended or adjusted under 35 U.S.C. 154(b) by 0 days.

(21) Appl. No.: 09/941,401

(22) Filed: Aug. 30, 2001

(65) Prior Publication Data

US 2003/0041368 A1 Mar. 6, 2003

(51) Int. Cl.[7] .............................. A41B 9/02; A41D 1/00
(52) U.S. Cl. .................................................. 2/403; 2/400
(58) Field of Search ............................ 2/403, 400, 401, 2/405, 402, 406, 408, 466, 912, 920; 450/133, 151; 482/124

(56) References Cited

U.S. PATENT DOCUMENTS

| | | | | | |
|---|---|---|---|---|---|
| 4,022,196 | A | * | 5/1977 | Clinton | 128/79 |
| 4,526,167 | A | * | 7/1985 | Ebenal | 128/158 |
| 4,622,962 | A | * | 11/1986 | Kauffman | 128/158 |
| 4,660,551 | A | * | 4/1987 | Nishimura | 128/79 |
| 4,961,419 | A | * | 10/1990 | Tribble et al. | 128/159 |
| 5,618,302 | A | * | 4/1997 | Martin | 606/201 |
| 5,716,319 | A | * | 2/1998 | Sembert | 600/38 |
| 5,728,043 | A | * | 3/1998 | Yong | 600/39 |
| 6,047,408 | A | * | 4/2000 | Brill, Jr. | 2/403 |
| 6,245,036 | B1 | * | 6/2001 | McRoberts et al. | 602/67 |
| 6,308,341 | B1 | * | 10/2001 | Shelton | 2/400 |
| 6,308,342 | B1 | * | 10/2001 | Qi | 2/403 |

* cited by examiner

*Primary Examiner*—John J. Calvert
*Assistant Examiner*—Alissa L. Hoey

(57) ABSTRACT

The invention is an Exercise Device that facilitates and enhances an exercise that improves male penile muscle condition causing firmer longer lasting erections with increased sensation and more powerful ejaculations. The device uses exercise rather than drugs or herbs to improve sexual pleasure for the male and female.

12 Claims, 3 Drawing Sheets

ULTIMATE WARE

BACKGROUND OF THE INVENTION

1. Field of Invention

This invention pertains to the subject matter of sexual health, sexual pleasure, and male sexual dysfunction.

2. Description of Prior Art

Muscle fiber will experience strength decline with age if they go unused. To maintain strength integrity, muscles must be exercised on a regular basis. (Men's Health, page 134, December 1998). Blood circulation decreases in inactive muscle tissue. Lack of penile muscle use may cause male sexual dysfunction along with many other causes.

The state of the technology addressing male dysfunction. and sexual enhancement has been to treat the problem chemically or with natural herbs. Drugs and herbs to address blood flow dysfunction in men come with many side effects as severe as death (Caverjet Product Information, Pharmacia & Upjohn Co., July 1997; Better Sex Naturally, Zachary Veillux, Men's Health, page 140, November 1998; The Year in Science, Sex, Sexual Chemistry, Rosie Mestel, Discover, page 32, January 1999; Lifestyle Drugs: What's After Viagra, Playboy, page 70, June 1999).

The invention at hand promotes penile blood circulation through natural and wholesome exercising. By exercising the erectile muscle tissue in the penis causes improved firmness, muscle strength, and longer lasting erections (Stronger Muscles, Better Sex, Men's Health, page 38, March 2000; Be One of the Geysers, Al Cooper, PhD., Men's Health, page 32, January/February 1998; Adapted from the book "A Lifetime of Sex", Stephen C. George, K. Winston Caine, Men's Health, page 110, March 1998). The benefit of using the invention to promote healthy exercise is that there are no side effects.

BRIEF SUMMARY OF THE INVENTION

The invention serves as a reminder and to promote exercise of erectile muscle tissue in the male penis. Erectile muscle is strengthened and blood flow is improved through regular exercise. Exercising contributes to increasing muscle health of the male reproductive apparatus thereby enhancing male and female sexual pleasure by firmer penis distention and more powerful ejaculations. The age-old problem of blood flow impotence in men is addressed.

DETAILED DESCRIPTION OF THE INVENTION

Figure 1:
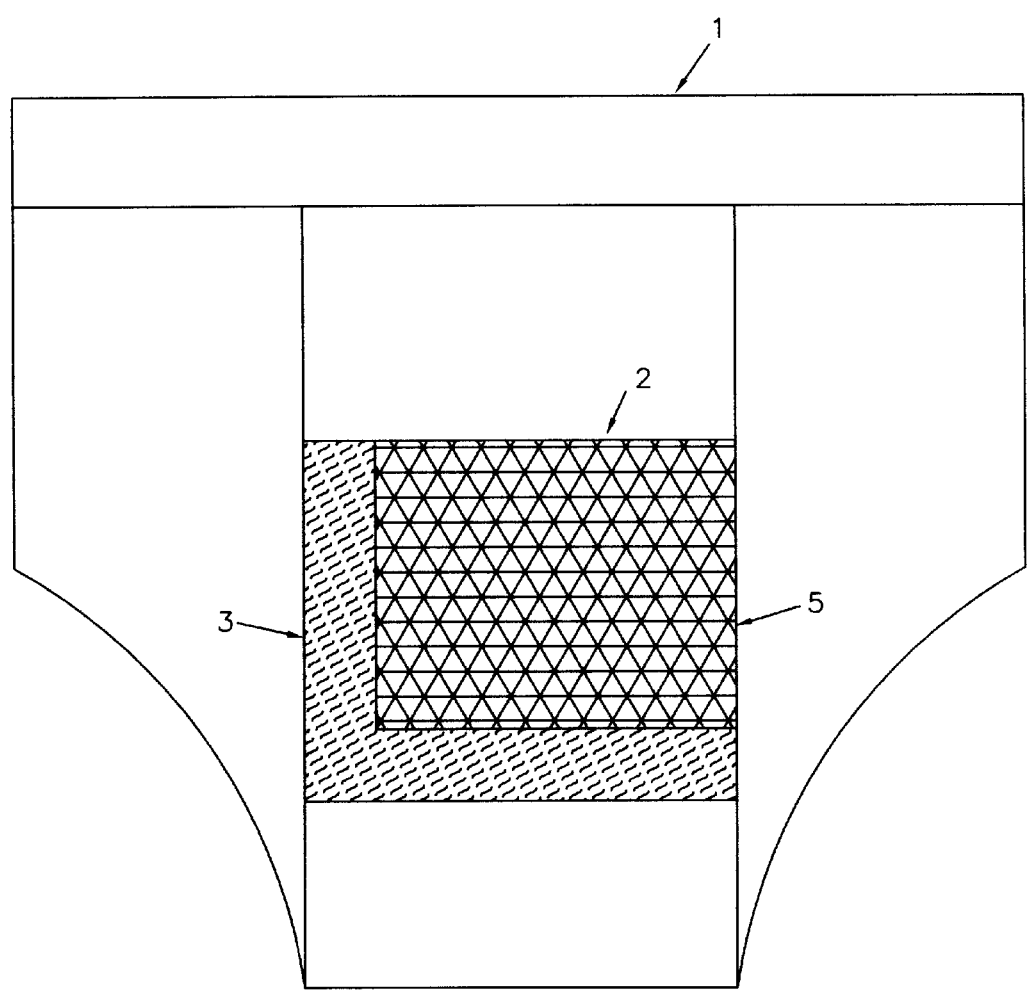
FIG. 1 is a frontal view of an undergarment according to the present invention.
Figure 2:
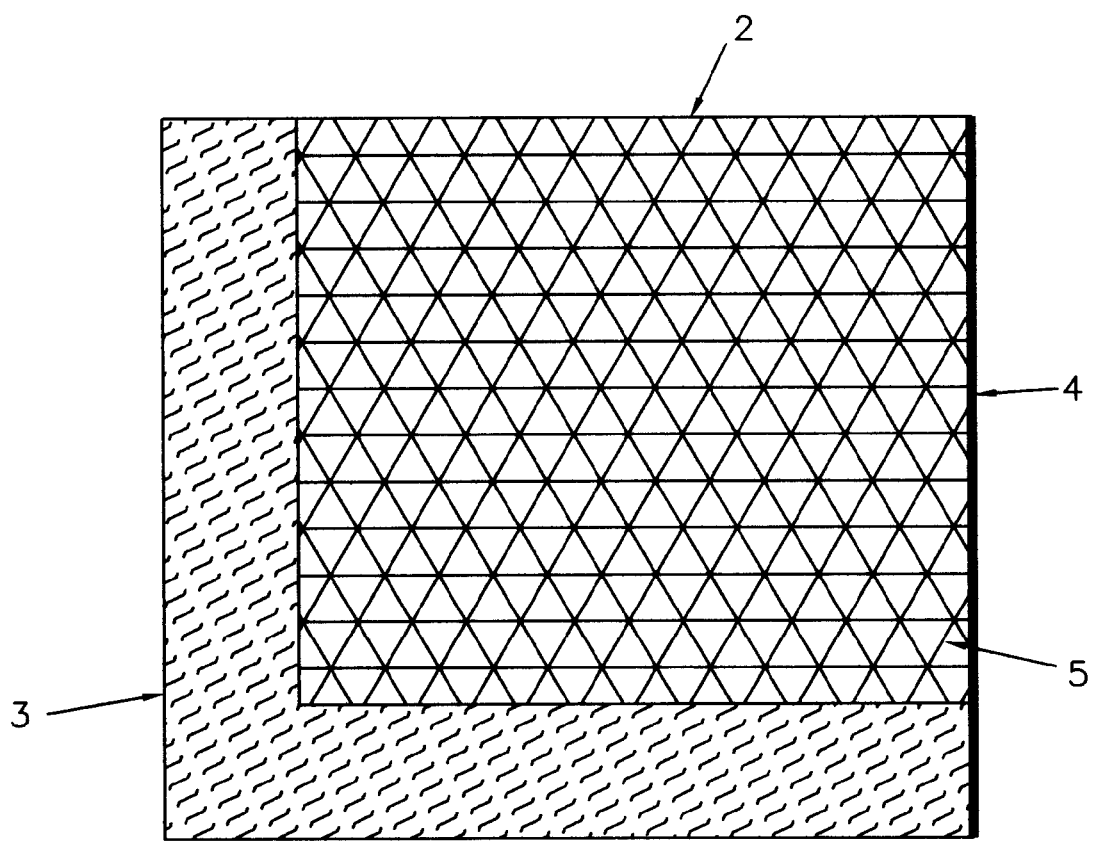
FIG. 2 is a front view of a cloth curtain shown in FIG. 1 and FIG. 3 to show details thereof.
Figure 3:
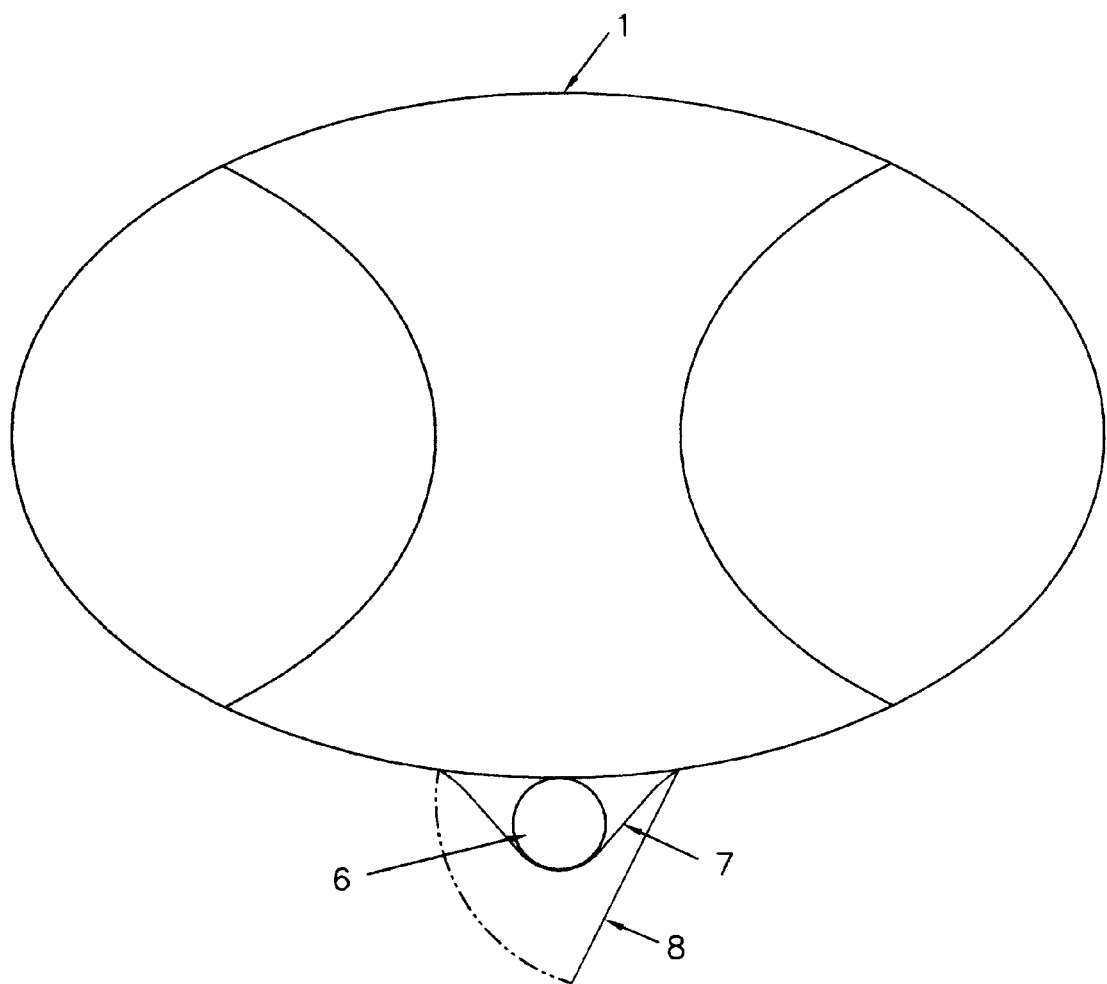
FIG. 3 is a top view of the undergarment showing a cloth curtain in open and closed positions.

The invention as shown in FIG. 1 shows an undergarment 1 which has a cloth curtain 2 attached to the front thereof. As shown in FIG. 1 and FIG. 2, the cloth curtain 2 has two pieces of hook-and-loop material 3 that is cut in a "U" shape being one half to one inch in width, having the uprights of the "U" being 6 inches in length and the base of the "U" being six inches from outside to outside. The two pieces of hook-and-loop material 3 are applied to each other as to fasten. One piece of the hook-and-loop fastener 3 is to be sewn to and undergarment 1, either on the outside as shown in FIGS. 1 and 3, or inside (not shown) but in a way that enables the placement of the male penis at its base inbetween the two mating layers of hook-and-loop fasteners 3. The cloth curtain 2 is made up of hook-and-loop straps 3 on the edges of a piece of fabric 5, which may be of any material compatible with the rest of the undergarment 1, such as cotton, stain, rayon, or similar material. A fabric line 4 is a seam of the cloth curtain 2.

To use the invention, as shown in FIG. 3, strap the penis inbetween the two hook-and-loop fastener straps at the base of the base of the penis. Starting in portion 8, the hook-and-loop fastener straps 3 and strapped around the penis 6 with moderate pressure as in position 7. While the penis 6 is in the strapped position 7, a wearer contracts the pubucoccygeal (PC) muscles (the same action used to stop urine flow during urination). Doing 20 rapid squeezes of the PC muscles at a time throughout the day will make the pubucoccygeal, corpora cavernosa, corpus spongiosum, penile epididymis muscle, ductus deferns muscle, bulbocavernosus muscles stronger enhancing erection and ejaculation of the wearer's male reproductive organ 6.

When the penis 6 is positioned inbetween secured and moderately constricted straps of hook-and-loop fasteners, as shown in FIG. 3 position 7, and kept in an up right position by the fabric of the cloth curtain 2. This fabric 5 may be of any compatible material, such as cotton, satin, rayon, or similar material. This position 7 and the moderate constriction enhance the exercise of muscle tissue in the penis's pubucoccygeal, corpora cavernosa, and corpus spongiosum (erectile tissue). Such exercise increases the erectile tissue's muscle strength and increases blood circulation to the fibrous tissue contained in erectile tissue. The invention that enhances exercise that promotes an increase in stimulation of the arteries carrying blood to the penis to dialate. With improved blood circulation, blood flows into the spaces of the fibrous tissues with an enhanced cause of distention and elevation of the penis. As the enhanced enlargement of the erectile tissue begins, the enhanced additional pressure causes the veins to be squeezed against the surrounding fibrous tissue and further diminishes the outflow of blood in the penis. This enhances the temporarily trapped blood in the penile organ with an increased pressure causing firmer and longer lasting erections.

The invention facilitates exercise that causes increased blood flow in the entire penile organ improves the sensory capabilities of penile nerves creating stronger nerve pulses; nerve pulses are responsible for the whole process of ejaculation.

The invention that enhances exercise that strengthens the muscle and blood flow of the muscles around the penile epididymis and ductus deferens (the tube extending from the epdidymis) are responsible for the emission stage of ejaculation. With increased muscle strength around the epdidymis and ductus deferens, contraction of the bulbocavernosus muscle is enhanced causing an improved ejaculation. The enhanced nerve response and increased muscle strength and blood flow of the bulbocavernosus muscle, the muscle responsible for ejaculation, cause an enhanced strength of spasmodic contractions of the bulbocavernosus muscle also.

The invention facilitates exercise that also assists the mucous-like secretions that first pass from the bulbourethral and urethral glands, and then the prostrate gland and seminal vesiclos to flush out the uretha before ejaculation in preparation of the uretha for sperm. The flushing of the uretha with more fluids after ejaculation is facilitated with the use of exercise.

What is claimed is:

1. A male undergarment with a front panel under which a penis of a wearer is lifted up, and as the front panel is re-attached to a hook and loop fastener adhering strip of the undergarment the penis is moderately constricted to continually remind the wearer to perform penile muscle strengthening exercises; thereby strengthening and toning penile muscle tissue creating firmer penis distention and elevation, and extending ejaculation.

2. An undergarment for a male wearer, comprising:
   the undergarment having a main body with a waist band and openings for legs;
   said main body also having an opening for a penis of the male wearer;
   a front panel that is hingeably detachable and re-attachable by means of a hook and loop fastener strip hingably covers the opening for the penis;
   said front panel is detached for locating the penis of the male wearer under said front panel and on top of said main body; and
   with the penis of the male wearer so located under said front panel, the penis is lifted by said front panel as said front panel is re-attached by the Velcro hook and loop fastener strip.

3. The undergarment of claim 2, wherein with said front panel re-attached, the penis of the wearer is moderately constricted such that the wearer may perform a penile muscle strengthening exercise against said front panel.

4. The undergarment of claim 2, wherein with said front panel re-attached, the penis of the wearer is moderately constricted such that the wearer is continually encouraged to perform a penile muscle exercise.

5. The undergarment of claim 2, wherein with said front panel re-attached, the penis of the wearer is moderately constricted such that the wearer is continually encouraged to perform a penile muscle exercise and continually provided with a resistance against which the wearer might strengthen a penile muscle.

6. The undergarment of claim 2, wherein the Velcro hook and loop fastener strip has an "L" shape.

7. The undergarment of claim 6, wherein with said front panel re-attached, the penis of the wearer is moderately constricted such that the wearer may perform a penile muscle strengthening exercise against said front panel.

8. The undergarment of claim 6, wherein with said front panel re-attached, the penis of the wearer is moderately constricted such that the wearer is continually encouraged to perform a penile muscle exercise.

9. The undergarment of claim 6, wherein with said front panel re-attached, the penis of the wearer is moderately constricted such that the wearer is continually encouraged to perform a penile muscle exercise and continually provided with a resistance against which the wearer might strengthen a penile muscle.

10. A method comprising the steps of:
    putting on an undergarment that has a main body made of fabric with an opening in the main body for a penis of a wearer to protrude;
    detaching a hingably connected front panel from a Velcro hook and loop fastener thereby allowing a penis of the wearer to be located between the main body and the front panel of the undergarment,
    re-attaching the hingably connected front panel to the hook and loop fastener, thereby lifting and moderately constricting the penis of the wearer; and
    strengthening a penile muscle by exercise against the moderate constricting of the front panel.

11. The method of claim 10, further comprising the step of stimulating increased blood circulation to a penile muscle by exercise against the moderate constriction of the front panel.

12. The method of claim 10, wherein exercise against the moderate constriction strengthens and tones penile muscle tissue creating firmer penis distention, elevation, and extending ejaculation.

* * * * *